(12) United States Patent
Clark et al.

(10) Patent No.: US 7,649,122 B2
(45) Date of Patent: Jan. 19, 2010

(54) ALKYLAROMATICS PRODUCTION

(75) Inventors: Michael C. Clark, Pasadena, TX (US); Vijay Nanda, Houston, TX (US)

(73) Assignee: ExxonMobile Chemical Patents Inc., Houston, TX (US)

( * ) Notice: Subject to any disclaimer, the term of this patent is extended or adjusted under 35 U.S.C. 154(b) by 138 days.

(21) Appl. No.: 11/599,864

(22) Filed: Nov. 15, 2006

(65) Prior Publication Data

US 2008/0139859 A1   Jun. 12, 2008

(51) Int. Cl.
C07C 2/58 (2006.01)

(52) U.S. Cl. ...................................... 585/467

(58) Field of Classification Search ................ 585/467
See application file for complete search history.

(56) References Cited

U.S. PATENT DOCUMENTS

| | | | |
|---|---|---|---|
| 3,449,070 A | 6/1969 | McDaniel et al. | |
| 3,751,506 A | 8/1973 | Burress | |
| 4,358,362 A | 11/1982 | Smith et al. | |
| 4,387,260 A | 6/1983 | Watson et al. | |
| 4,429,176 A | 1/1984 | Chester et al. | |
| 4,522,929 A | 6/1985 | Chester et al. | |
| 4,826,667 A | 5/1989 | Zones et al. | |
| 4,954,325 A | 9/1990 | Rubin et al. | |
| 5,030,786 A | 7/1991 | Shamshoum et al. | |
| 5,077,445 A | 12/1991 | Le | |
| 5,081,323 A | 1/1992 | Innes et al. | |
| 5,177,285 A | 1/1993 | Van Opdorp et al. | |
| 5,191,135 A | 3/1993 | Dwyer et al. | |
| 5,198,595 A | 3/1993 | Lee et al. | |
| 5,371,310 A * | 12/1994 | Bennett et al. | 585/467 |
| 5,998,684 A | 12/1999 | Ho et al. | |
| 6,313,362 B1 | 11/2001 | Green et al. | |
| 6,355,851 B1 | 3/2002 | Wu et al. | |
| 6,512,153 B1 | 1/2003 | Cappellazzo et al. | |
| 6,525,234 B1 | 2/2003 | Dandekar et al. | |
| 6,909,026 B2 | 6/2005 | Dandekar et al. | |
| 2004/0192985 A1 | 9/2004 | Smith | |
| 2004/0267066 A1 | 12/2004 | Smith | |

FOREIGN PATENT DOCUMENTS

| | | |
|---|---|---|
| EP | 0 064 046 | 11/1982 |
| EP | 0 537 389 | 4/1993 |
| EP | 0 538 518 | 4/1993 |
| EP | 0 842 914 | 5/1998 |
| JP | 11035497 | 2/1999 |
| JP | 11035498 | 2/1999 |
| WO | 02/14240 | 2/2002 |

OTHER PUBLICATIONS

U.S. Appl. No. 11/343,868, filed Jan. 31, 2006, Clark.

* cited by examiner

*Primary Examiner*—Thuan Dinh Dang
(74) *Attorney, Agent, or Firm*—D M Tyus

(57) ABSTRACT

A process for alkylation of an alkylatable aromatic compound to produce a monoalkylated aromatic compound, comprising the steps of (a) contacting at least one the alkylatable aromatic compound and at least one the alkylating agent with at least one molecular sieve catalyst under suitable alkylation or transalkylation conditions in at least one reaction zone, to produce at least one effluent which comprises the monoalkylated aromatic compound, wherein the suitable alkylation or transalkylation conditions comprise a water content being in a range from about 1 wppm to about 10 wt. % based on the combined weight of the alkylatable aromatic compound and the alkylating agent; and (b) maintaining the water content in the reaction zone; wherein the cycle length of the molecular sieve catalyst operated inside the range of the water content is greater than the cycle length of the molecular sieve catalyst operated outside the range of the water content.

7 Claims, No Drawings

ALKYLAROMATICS PRODUCTION

FIELD

The present invention relates to a process for producing alkylated aromatic products, particularly ethylbenzene and cumene. In particular this disclosure provides a process for extending the life of a molecular sieve catalyst useful for alkylation of aromatics.

BACKGROUND

Hydrocarbon conversion processes using catalysts are often subject to catalyst regeneration and replacement requirements resulting from "poisoning" or "deactivation" of the catalyst by one or more impurities contained in the hydrocarbon feedstock. Short catalyst cycle length often results in both more frequent catalyst regeneration requirements and reduced ultimate life of the catalyst before replacement is necessary. Catalyst replacement often involves a process shutdown, lost production, and significant costs. In many cases, catalyst cycle length needs to be improved by preventing coke-forming and/or reducing "poisoning". Various processes have been developed for removal of such impurities prior to contact with the catalyst.

Alkyl aromatic compounds such as cumene and ethylbenzene are often produced by reaction of aromatics and olefins in the presence of acidic molecular sieve catalysts. Liquid phase operation of aromatics alkylation processes has often been found to result in reduced operating costs as well as fewer undesirable byproducts than earlier vapor phase technologies.

Catalysts that can be used for alkylation of benzene with ethylene/propylene and also for transalkylation of benzene and polyethylbenzenes/polyisopropylbenzenes in liquid phase include zeolite beta, zeolite Y, zeolite omega, ZSM-5, ZSM-12, MCM-22, MCM-36, MCM-49, MCM-56, MCM-58, MCM-68, Faujasite, Mordenite, porous crystalline magnesium silicates, and tungstate modified zirconia, all of which are known in the art.

Water as one of the impurities in the feed may impact the activity, selectivity, and the life of the molecular sieve catalyst. During the alkylation/transalkylation processes, the catalyst ages due to the deposition of coke and other deleterious materials on the catalyst. Such catalyst aging causes a decrease in the catalyst's activity for the conversion of reactants to products. To restore a catalyst's activity, the catalyst is often regenerated by controlled oxidation in air, or by other means. Following regeneration, the catalyst's activity is restored to a certain degree. However, the regenerated catalyst often has a reduced selectivity and activity to produce the desired monoalkylated compound, and increased amounts of the more undesirable polyalkylated impurities are produced. Therefore, there is a need for improved alkylation and/or transalkylation catalyst life. We surprisingly found that the catalyst life of an alkylation and/or translation catalyst may be improved by co-feeding water.

SUMMARY OF THE INVENTION

In some embodiments, this disclosure relates to a process for alkylation of an alkylatable aromatic compound to produce a monoalkylated aromatic compound, comprising the steps of:

(a) contacting at least one the alkylatable aromatic compound and at least one the alkylating agent with at least one molecular sieve catalyst under suitable alkylation or transalkylation conditions in at least one reaction zone, to produce at least one effluent which comprises the monoalkylated aromatic compound, wherein the suitable alkylation or transalkylation conditions comprise a water content being in a range from about 1 wppm to about 10 wt. %, preferably from 1 wppm to less than 1 wt. %, preferably from 1 wppm to less than 500 wppm, preferably from 1 wppm to less than 100 wppm, preferably from 1 wppm to less than 50 wppm, based on the combined weight of the alkylatable aromatic compound and the alkylating agent; and (b) maintaining the water content in the reaction zone;

wherein the cycle length of the molecular sieve catalyst operated inside the range of the water content is greater than the cycle length of the molecular sieve catalyst operated outside the range of the water content when said reaction zone is operated under equivalent alkylation or transalkylation conditions.

In some aspects of this disclosure, the molecular sieve catalyst comprises a molecular having a Constraint Index of less than 12, optionally, less than 2. In a preferred embodiment, the catalyst consists essentially of a MCM-22 family molecular sieve, preferably the molecular sieve is ERB-1, ITQ-1, ITQ-2, ITQ-30, PSH-3, SSZ-25, MCM-22, MCM-36, MCM-49, MCM-56, or a MCM-22 family material. In one embodiment, the catalyst comprises a molecular selected from a group consisting of zeolite beta, zeolite Y, Ultrastable Y, Dealuminized Y, rare earth exchanged Y, mordenite, TEA-mordenite, ERB-1, ITQ-1, ITQ-2, ITQ-30, PSH-3, SSZ-25, MCM-22, MCM-36, MCM-49, MCM-56, silicalite, ZSM-3, ZSM-4, ZSM-5, ZSM-11, ZSM-12, ZSM-14, ZSM-18, ZSM-20, ZSM-22, ZSM-23, ZSM-35, and ZSM-48.

In other aspects of this disclosure, the suitable alkylation or transalkylation conditions include a temperature from about 100° C. to about 400° C., a pressure from about 20.3 to 4500 kPa-a, a WHSV from about 0.1 to about 10 h$^{-1}$, and a molar ratio of the alkylatable compound over the alkylating agent from about 0.1:1 to 50:1. In a preferred embodiment, the suitable alkylation or transalkylation conditions maintain the reaction zone under at least partial liquid phase conditions.

In one embodiment, the monoalkylated aromatic compound comprises ethylbenzene, the alkylatable aromatic compound comprises benzene, and the alkylating agent comprises ethylene. In another embodiment, the monoalkylated aromatic compound comprises cumene, the alkylatable aromatic compound comprises benzene, and the alkylating agent comprises propylene. In yet another embodiment, the monoalkylated aromatic compound comprises sec-butylbenzene, the alkylatable aromatic compound comprises benzene, and the alkylating agent comprises butene.

In some embodiments, this disclosure relates to a process for alkylation of benzene with ethylene to produce ethylbenzene. In other embodiments, this disclosure relates to a process for alkylation of benzene with propylene to produce cumene.

These and other facets of the present invention shall become apparent from the following detailed description and appended claims.

DETAILED DESCRIPTION OF THE PREFERRED EMBODIMENTS

Introduction

All patents, patent applications, test procedures, priority documents, articles, publications, manuals, and other documents cited herein are fully incorporated by reference to the extent such disclosure is not inconsistent with the present invention and for all jurisdictions in which such incorporation is permitted.

When numerical lower limits and numerical upper limits are listed herein, ranges from any lower limit to any upper limit are contemplated.

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology". A unit cell is a spatial arrangement of atoms which is tiled in three-dimensional space to describe the crystal as described in the "Atlas of Zeolite Framework Types", Fifth edition, 2001, the entire content of which is incorporated as reference;

(ii) molecular sieves made from a common second degree building block, a 2-dimensional tiling of such MWW framework type unit cells, forming a "monolayer of one unit cell thickness", preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion, and any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575) and MCM-56 (described in U.S. Pat. No. 5,362,697). The entire contents of the patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of the molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstroms.

As used herein, an "alkylatable aromatic compound" is a compound that may receive an alkyl group and an "alkylating agent" is a compound which may donate an alkyl group to an alkylatable aromatic compound. One example of the alkylatable aromatic compounds is benzene. Examples of the alkylating agent are ethylene, propylene, polyalkylated aromatic compound(s), e.g., di-ethylbenzene, tri-ethylbenzene, di-isopropylbenzene, and tri-isopropylbenzene The term "wppm" as used herein is defined as parts per million by weight.

The term "aromatic" as used herein is to be understood in accordance with its art-recognized scope which includes alkyl substituted and unsubstituted mono- and polynuclear compounds. Compounds of an aromatic character, which possess a heteroatom, are also useful provided sufficient activity can be achieved if they act as catalyst poisons under the reaction conditions selected.

The term "at least partially in liquid phase" as used herein is understood as a mixture having at least 1 wt. % liquid phase, optionally at least 5 wt. % liquid phase at a given temperature, pressure, and composition.

The term "cycle length" as used herein means the total on-oil time between regenerations, or the on-oil time period between fresh load and regeneration. After the fresh catalyst or the regenerated catalyst being brought on-oil, the catalyst may be deactivated due to coke deposition or poison. The reaction zone has to be operated at a higher temperature to maintain the same productivity or catalytic activity. The catalyst has to be regenerated once the reaction zone temperature reaching a threshold temperature, typically determined by metallurgy of the reactor or some economic factors.

The term "on-oil" as used herein is to be understood as the catalyst being brought under alkylation or transalkylation conditions. The alkylation or transalkylation conditions include temperature, pressure, alkylatable aromatic compound(s), alkylating agent(s), and WHSV, which are suitable to covert at least 1 wt. %, preferably at least 10 wt. % of the alkylatable aromatic compound(s) (based on the total alkylatable aromatic compound(s) in the feed) to the monoalkylated aromatic compound(s).

The water content as used in this disclosure means the weight ppm (wppm) or weight percentage (wt. %) of water based on the total weight of the combined alkylatable aromatic compound and alkylating agent in the reaction zone.

Feedstocks and Products

Substituted aromatic compounds which may be used for the invention should possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic compounds that may be used for this disclosure include benzene, naphthalene, anthracene, naphthacene, perylene, coronene, and phenanthrene, with benzene being preferred.

Suitable alkyl substituted aromatic compounds that may be used for this disclosure include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate streams that may contain substantial quantities of benzene, toluene and/or xylene may be particularly suitable feed for the process of this disclosure. Although the process is particularly directed to the production of ethylbenzene from polymer grade and dilute ethylene, it is equally applicable to the production of other $C_7$-$C_{20}$ alkylaromatic compounds, such as cumene, as well as $C_6$+ alkylaromatics, such as $C_8$-$C_{16}$ linear and near linear alkylbenzenes.

Suitable alkylating agent(s) that may be used in this disclosure comprise alkene compound(s), alcohol compound(s), and/or alkylbenzene(s), and mixtures thereof. Other suitable alkylating agents that may be useful in the process of this disclosure generally include any aliphatic or aromatic organic compound having one or more available alkylating aliphatic groups capable of reaction with the alkylatable aromatic compound. Examples of suitable alkylating agents are $C_2$-$C_{16}$ olefins such as $C_2$-$C_5$ olefins, viz., ethylene, propylene, the butenes, and the pentenes; $C_1$-$C_{12}$ alkanols (inclusive of monoalcohols, dialcohols, trialcohols, etc.), preferably $C_1$-$C_5$ alkanols, such as methanol, ethanol, the propanols, the butanols, and the pentanols; $C_2$-$C_{20}$ ethers, e.g., $C_2$-$C_5$ ethers including dimethylether and diethylether; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, polyalkylated aromatic compound(s), e.g., bi-alkylated benzenes (e.g., bi-ethylbenzene (s) or bi-isopropylbenzenes) and tri-alkylated benzene(s) (e.g., tri-ethylbenzenes or tri-isopropylbenzenes), and so forth. Thus the alkylating agent may preferably be selected from the group consisting of $C_2$-$C_5$ olefins, $C_1$-$C_5$ alkanols, bi-ethylbenzene(s), bi-isopropylbenzene(s), tri-ethylbenzene (s) and/or tri-isopropylbenzene(s). The alkylating agent includes a concentrated alkene feedstock (e.g., polymer grade olefins) and a dilute alkene feedstock (e.g., catalytic cracking off-gas).

In one embodiment, the feed(s) comprising the alkylatable aromatic compound(s) and/or alkylating agent(s) may include water. In another embodiment, the water content in a reaction zone may be adjusted and/or controlled by the addition of water. In one aspect, a feed comprising liquid water, steam, or a mixture thereof, may be co-fed with the alkylatable aromatic compound and/or alkylating agent to the reaction zone. The amount of water contained in the alkylatable aromatic compound and/or alkylating agent with a co-feed of liquid water and/or steam and/or a mixture thereof is such that the water content in a reaction zone is in a range between a lower limit and a higher limit, i.e., more than or equal to a lower limit and less than or equal to a higher limit. The following water contents are useful for lower water content limits: 1 wppm, 5 wppm, 10 wppm, 50 wppm, 100 wppm, 200 wppm, 300 wppm, 400 wppm, 500 wppm, 1000 wppm. The low limit is about 1 wppm, or 10 wppm. The following water contents are useful for higher water content limits: 10 wt. %, 5 wt. %, 2.5 wt. %, 1 wt. %, 500 wppm, 200 wppm, 100 wppm, 50 wppm, or 10 wppm.

In another embodiment, the water content of the reaction zone is adjusted and/or controlled by removing water from the alkylatable aromatic compound and/or alkylating agent that is fed to the reaction zone. For example, the alkylatable aromatic compound and/or alkylating agent may be dried by a molecular sieve bed before feeding to the reaction zone.

By maintaining, adjusting, and/or controlling the amount of water in combined feed(s) of the alkylatable aromatic compound and/or alkylating agent to a desired range of the water content, the cycle length of the molecular sieve catalyst operated within the range of the water content of this disclosure improves by at least 1%, preferably, at least 10%, more preferably at least 50%, even more preferably at least 100% as comparing to the cycle length of the molecular sieve catalyst operated outside the range of the water content of this disclosure when said reaction zone is operated under equivalent alkylation or transalkylation conditions. Water content in the reaction zone may be measured by conventional techniques, such as, GC, GC/MS, or other suitable techniques known to a skilled artisan.

Suitable alkyl substituted aromatic compounds which may be prepared from the alkylation process of the present invention include toluene, xylene, isopropylbenzene (cumene), normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethyl,anthracene; 9-ethylanthracene; 2-methylanthracene; o-methylanthracene; 9,10-dimethylphenanthrene; and 3-methyl-phenanthrene. Preferably, the alkylated aromatic product comprises monoalkylbenzene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{16}$.

Reaction Conditions

Typical aromatic alkylation reactions which may be improved the present invention include obtaining ethylbenzene from the reaction of benzene with ethylene, cumene from the reaction of benzene with propylene, ethyltoluene from the reaction of toluene with ethylene, and cymenes from the reaction of toluene with propylene.

The reaction zone is maintained for the majority of the on-oil time with a water content in a range between a lower limit and a higher limit, i.e., more than or equal to a lower limit and less than or equal to a higher limit. The following water contents are useful for lower water content limits: 1 wppm, 5 wppm, 10 wppm, 50 wppm, 100 wppm, 200 wppm, 300 wppm, 400 wppm, 500 wppm, 1000 wppm. The low limit is about 1 wppm, or 10 wppm. The following water contents are useful for higher water content limits: 10 wt. %, 5 wt. %, 2.5 wt. %, 1 wt. %, 500 wppm, 200 wppm, 100 wppm, 50 wppm, or 10 wppm. The term "majority of the on-oil time" as used herein, means at least 50%, preferably at least 60%, more preferably at least 70%, even more preferably at least 80%, most preferably at least 90%, of the on-oil time. The term "on-oil" time as used herein, means the cumulative time when the catalyst is in contact with alkylatable aromatic compound(s) and/or alkylating agent(s) under alkylation/transalkylation conditions.

The reactants can be in either the vapor phase or the liquid phase and can be neat, i.e., free from intentional admixture or dilution with other material, or they can be brought into contact with the molecular sieve catalyst composition with the aid of carrier gases or diluents such as, for example, hydrogen or nitrogen.

When benzene is alkylated with ethylene to produce ethylbenzene, the alkylation reaction may be carried out in the liquid phase. Suitable liquid phase conditions include a temperature between about 150° C. and 316° C., preferably between about 205° C. and 260° C., a pressure up to about 20875 kPa-a, preferably between 2860 and 5600 kPa-a, a space velocity between about 0.1 and 20 $h^{-1}$ WHSV, preferably between 1 and 6 $h^{-1}$ WHSV, based on the ethylene feed, and a ratio of the benzene to the ethylene in the alkylation reactor from 1:1 to 30:1 molar, preferably from about 1:1 to 10:1 molar.

When benzene is alkylated with propylene to produce cumene, the reaction may also take place under liquid phase conditions including a temperature of up to about 250° C., e.g., up to about 150° C., e.g., from about 10° C. to about 125° C.; a pressure of about 25000 kPa-a or less, e.g., from about 101 to about 3000 kPa-a; and an aromatic hydrocarbon weight hourly space velocity (WHSV) of from about 5 $hr^{-1}$ to about 250 $hr^{-1}$, preferably from 5 $hr^{-1}$ to 50 $hr^{-1}$.

The alkylation reaction may also take place with the alkylatable aromatic compound and the alkylating agent in the reaction zone under conditions of at least partially in liquid phase. The alkylation or transalkylation conditions include a temperature of 100 to 285° C. and a pressure of 689 to 4601 kPa-a, preferably, a pressure of 1500 to 3000 kPa-a, a WHSV based on alkylating agent (e.g., alkene) for overall reactor of 0.1 to 10 $h^{-1}$, preferably, 0.2 to 2 $h^{-1}$, more preferably, 0.5 to 1 $hr^{-1}$, or a WHSV based on both alkylating agent and alkylatable aromatics for overall reactor of 10 to 100 $h^{-1}$, preferably, 20 to 50 $h^{-1}$. The alkylatable aromatic compound is alkylated with the alkylating agent (e.g., alkene) in the presence of an alkylation or transalkylation catalyst in a reaction zone or a plurality of reaction zones. The reaction zone(s) are preferably located in a single reactor vessel, but may include another reaction zone having an alkylation or transalkylation catalyst bed, located in separate vessel which may be a by-passable and which may operate as a reactive guard bed. The catalyst composition used in the reactive guard bed may be different from the catalyst composition used in the reaction zone. The catalyst composition used in the reactive guard bed may have multiple catalyst compositions. At least one reaction zone, and normally each reaction zone, is maintained under conditions effective to cause alkylation of the alkylatable aromatic compound with the alkylating agent in the presence of an alkylation or transalkylation catalyst.

Particular conditions for carrying out the alkylation of benzene with ethylene at least partially in liquid phase may have a temperature of from about 120 to 285° C., preferably, a temperature of from about 150 to 260° C., a pressure of 689 to 4601 kPa-a, preferably, a pressure of 1500 to 4137 kPa-a, a WHSV based on total ethylene and total catalyst for overall reactor of 0.1 to 10 $h^{-1}$, preferably, 0.2 to 2 $h^{-1}$, more preferably, 0.5 to 1 $h^{-1}$, or a WHSV based on both total ethylene and benzene, and total catalyst for overall reactor of 10 to 100 $h^{-1}$, preferably, 20 to 50 $h^{-1}$, and a molar ratio of benzene to ethylene from about 1 to about 10.

Particular conditions for carrying out the at least partially in liquid phase alkylation of benzene with propylene may include a temperature of from about 80 to 160° C., a pressure of about 680 to about 4800 kPa-a; preferably from about 100 to 140° C. and pressure of about 2000 to 3000 kPa-a, a WHSV based on propylene of from about 0.1 about 10 $hr^{-1}$, and a molar ratio of benzene to ethylene from about 1 to about 10.

The effluent from the reaction zone comprises the desired alkylated aromatic product, unreacted alkylatable aromatic compound, any unreacted alkylating agent (e.g., alkene, alkene conversion is expected to be at least 90 mol. %, preferably, about 98-99.9999 mol. %) and the alkane component and the other impurities. In one embodiment, at least a portion of the effluent is fed to another reaction zone where an alkylating agent is added for reaction with the unreacted alkylatable aromatic compound with an alkylation or transalkylation catalyst. Furthermore, at least a portion the effluent from any of the reaction zone(s) may be fed directly or indirectly to a transalkylation unit.

In addition to, and upstream of, the reaction zones, a by-passable reactive or unreactive guard bed may normally be located in a reactor separate from the alkylation reactor. Such guard bed may also be loaded with an alkylation or transalkylation catalyst, which may be the same or different from the catalyst used in the reaction zone(s). Such guard bed is maintained from under ambient conditions, or at suitable alkylation or transalkylation conditions. At least a portion of alkylatable aromatic compound, and optionally at least a portion of the alkylating agent, are passed through the unreactive or reactive guard bed prior to entry into the reaction zone. These guard beds not only serve to affect the desired alkylation reaction, but is also used to remove any reactive impurities in the feeds, such as nitrogen compounds, which could otherwise poison the remainder of the alkylation or transalkylation catalyst. The catalyst in the reactive or unreactive guard bed is therefore subject to more frequent regeneration and/or replacement than the remainder of the alkylation or transalkylation catalyst, and hence the guard bed is typically provided with a by-pass circuit so that the alkylation feed(s) may be fed directly to the series connected reaction zones in the reactor while the guard bed is out of service. The reactive or unreactive guard bed may be operated in co-current upflow or downflow operation.

The reaction zone(s) used in the process of the present invention is typically operated so as to achieve essentially complete conversion of the alkene. However, for some applications, it may be desirable to operate at below 100% alkene conversion. The employment of a separate finishing reactor downstream of the reaction zone(s) may be desirable under certain conditions. The finishing reactor would also contain alkylation or transalkylation catalyst, which could be the same or different from the catalyst used in other reaction zones in the alkylation or transalkylation reactor(s) and may be maintained under at least partially liquid phase or alternately vapor phase alkylation or transalkylation conditions. The polyalkylated aromatic compounds in the effluents may be separated for transalkylation with alkylatable aromatic compound(s). The alkylated aromatic compound is made by transalkylation between polyalkylated aromatic compounds and the alkylatable aromatic compound.

The alkylation or transalkylation reactor(s) used in the process of the present invention may be highly selective to the desired monoalkylated product, such as ethylbenzene, but typically produces at least some polyalkylated species. In one embodiment, the effluent from the final alkylation reaction zone is subjected to a separation step to recover polyalkylated aromatic compound(s). In another embodiment, at least a portion of the polyalkylated aromatic compound is supplied to a transalkylation reactor which may be separate from the alkylation reactor. The transalkylation reactor produces an effluent which contains additional monoalkylated product by reacting the polyalkylated species with an alkylatable aromatic compound. At least a portion of these effluents may be separated to recover the alkylated aromatic compound (monoalkylated aromatic compound and/or polyalkylated aromatic compound).

Where the alkylation system includes a reactive guard bed, it is maintained under at least partial in liquid phase conditions. The guard bed will preferably operate at a temperature of from about 120 to 285° C., preferably, a temperature of from about 150 to 260° C., a pressure of 689 to 4601 kPa-a), preferably, a pressure of 1500 to 4137 kPa-a, a WHSV based on total ethylene and the total amount of catalyst for the overall reactor of 0.1 to 10 $h^{-1}$, preferably, 0.2 to 2 $h^{-1}$, more preferably, 0.5 to 1 $h^{-1}$, or a WHSV based on both total ethylene and total benzene, and the total amount of catalyst for the overall reactor of 10 to 100 $h^{-1}$, preferably, 20 to 50 $h^{-1}$, and a molar ratio of benzene to ethylene from about 1 to about 10.

The transalkylation reaction may take place under at least partially in liquid phase conditions. Particular conditions for carrying out the at least partially in liquid phase transalkylation of polyalkylated aromatic compound(s), e.g., polyethylbenzene(s) or polyisopropylbenzene(s), with benzene may include a temperature of from about 100° to about 300° C., a pressure of 696 to 4137 kPa-a (101 to 600 psia), a WHSV based on the weight of the polyalkylated aromatic compound (s) feed to the alkylation reaction zone of from about 0.5 to about 100 $hr^{-1}$ and a molar ratio of benzene to polyalkylated aromatic compound(s) of from 1:1 to 30:1, preferably, 1:1 to 10:1, more preferably, 1:1 to 5:1.

In another embodiment, the transalkylation reaction may take place under vapor phase conditions. Particular conditions for carrying out the vapor phase transalkylation of polyalkylated aromatic compound(s), e.g., polyethylbenzene(s) or polyisopropylbenzene(s), with benzene may include a temperature of from about 350 to about 450° C., a pressure of 696 to 1601 kPa-a (101 to 232 psia), a WHSV based on the weight of the polyalkylated aromatic compound(s) feed to the reaction zone of from about 0.5 to about 20 $hr^{-1}$, preferably, from about 1 to about 10 $hr^{-1}$, and a molar ratio of benzene to polyalkylated aromatic compound(s) of from 1:1 to 5:1, preferably, 2:1 to 3:1.

Catalysts

It will be understood by a person skilled in the art that the MCM-22 family material may contain impurities, such as amorphous materials; unit cells having non-MWW framework topologies (e.g., MFI, MTW); and/or other impurities (e.g., heavy metals and/or organic hydrocarbons). The MCM-22 family materials of this disclosure are preferably substantially free of non-MCM-22 family material(s). The term "substantially free of non-MCM-22 family material(s)" used herein means the MCM-22 family material of this disclosure preferably contains a minor proportion (less than 50 wt %), preferably less than 20 wt %, more preferably less than 10 wt %, even more preferably less than 5 wt %, and most preferably less than 1 wt %, of non-MCM-22 family materials ("impurities") in the MCM-22 family materials, which weight percent (wt %) values are based on the combined weight of impurities and pure phase MCM-22 family materials.

In some embodiments, the crystalline MCM-22 family molecular sieve of this disclosure comprises at least one of MCM-22, MCM-49, MCM-56, ITQ-1, ITQ-3, an intergrowth-phase thereof, or a mix phase thereof. In a preferred embodiment of this disclosure, the catalyst composition of this disclosure has at least 1 wt. %, preferably at least 10 wt. %, more preferably at least 50 wt. %, even more preferably at least 65 wt. %, of the crystalline MCM-22 family molecular sieve based on the total weight of the catalyst composition.

In one embodiment of this disclosure, the alkylation or transalkylation catalyst that may be used in this disclosure is a porous crystalline molecular sieve having a zeolite framework type of at least one of MWW, FAU, *BEA, and any combination thereof. In another embodiment, the porous crystalline material comprises at least one of zeolite beta, zeolite Y, Ultrastable Y (USY), Dealuminized Y (Deal Y), mordenite, ERB-1, ITQ-1, ITQ-2, ITQ-30, rare earth exchanged Y (REY), PSH-3, SSZ-25, MCM-22, MCM-36, MCM-49, MCM-56, or a MCM-22 family material.

Alternatively, the alkylation and/or transalkylation catalyst may further comprise a medium pore molecular sieve having a Constraint Index of 2-12 (as defined in U.S. Pat. No. 4,016, 218), including ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234, 231. The entire contents of all the above patent specifications are incorporated herein by reference.

In another embodiment, the alkylation and/or transalkylation catalyst may comprise a large pore molecular sieve having a Constraint Index of less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104. The entire contents of all the above patent specifications are incorporated herein by reference.

The Constraint Index is a convenient measure of the extent to which an aluminosilicate or molecular sieve provides controlled access to molecules of varying sizes to its internal structure. For example, aluminosilicates which provide a highly restricted access to and egress from its internal structure have a high value for the constraint index, and aluminosilicates of this kind usually have pores of small size, e.g. less than 5 Angstroms. On the other hand, aluminosilicates which provide relatively free access to the internal aluminosilicate structure have a low value for the constraint index, and usually pores of large size. The method by which Constraint Index may be determined is described fully in U.S. Pat. No. 4,016,218, which is incorporated herein by reference.

Although the invention is not intended to be limited to any theory of operation, it is believed that addition of water to the reaction zone may prevent or slow the process of catalyst coking or poison. One theory is that some catalyst poison components may be dissolved in the water. Another theory is that water may replace some of the poison components already adsorbed on the active surface of the catalyst. Yet another theory is that water may interact with the catalyst active site and prevent the formation of coke/coke precursor (s).

The present disclosure may find applications in the process of alkylation or transalkylation of an alkylatable aromatic compound to produce a monoalkylated aromatic compound. Examples of these processes are manufacture of ethylbenzene or cumene.

We claim:

1. A process for alkylation of benzene with ethylene to produce ethylbenzene, comprising the steps of:
   (a) contacting said benzene and said ethylene with at least one catalyst comprising a MCM-22 molecular sieve under suitable conditions in at least one reaction zone, to produce at least one effluent which comprises said ethylbenzene, wherein said suitable conditions comprise a water content being in a range from about 1 wppm to about 10 wt. % based on the combined weight of said benzene and said ethylene; and
   (b) maintaining said water content in said reaction zone for the majority of the on-oil time by removing water from at least one of said alkylatable aromatic compound or said alkylating agent;
wherein the cycle length of said molecular sieve catalyst operated inside said range of said water content is greater than the cycle length of said molecular sieve catalyst operated outside said range of said water content when said reaction zone is operated under equivalent conditions, wherein said suitable conditions include a temperature from about 100° C. to about 400° C., a pressure from about 20.3 to 4500 kPa-a, a WHSV from about 0.1 to about 10 $h^{-1}$, and a molar ratio of said benzene over said ethylene from about 0.1:1 to 50:1.

2. The process of claim 1, wherein said range of said water content is less than about 1 wt. %.

3. The process of claim 1, wherein said water content of said reaction zone is less than about 500 wppm.

4. The process of claim 1, wherein said water content of said reaction zone is less than about 100 wppm.

5. The process of claim 1, wherein said water content of said reaction zone is less than about 50 wppm.

6. The process of claim 1, further comprising a finishing reactor downstream of said reaction zone.

7. The process of claim 1, wherein said suitable conditions maintain said reaction zone under at least partial liquid phase conditions.

* * * * *